United States Patent
Duffy et al.

(10) Patent No.: US 12,351,540 B2
(45) Date of Patent: Jul. 8, 2025

(54) PROCESS FOR PREPARING CYANOACETATES

(71) Applicant: Henkel AG & Co. KGaA, Duesseldorf (DE)

(72) Inventors: Cormac Duffy, County Louth (IE); Justine O'Sullivan, County Kildare (IE); Ciara Goff, County Wexford (IE); Umar Farid, County Dublin (IE); Jessica Ramos, County Kildare (IE); Michael Thai Trung King, Dublin (IE); Isidro Cobo Cardenete, Dublin (IE); Marisa Phelan, Dublin (IE); Barry Burns, Dublin (IE)

(73) Assignee: Henkel AG & Co. KGaA, Duesseldorf (DE)

( * ) Notice: Subject to any disclaimer, the term of this patent is extended or adjusted under 35 U.S.C. 154(b) by 796 days.

(21) Appl. No.: 17/503,897

(22) Filed: Oct. 18, 2021

(65) Prior Publication Data

US 2022/0033350 A1    Feb. 3, 2022

Related U.S. Application Data

(63) Continuation of application No. PCT/EP2020/060884, filed on Apr. 17, 2020.

(30) Foreign Application Priority Data

Apr. 18, 2019 (GB) .................. 1905576

(51) Int. Cl.
*C07C 253/06* (2006.01)
*C07C 253/00* (2006.01)
*C07C 253/30* (2006.01)
*C07C 253/34* (2006.01)

(52) U.S. Cl.
CPC .......... *C07C 253/06* (2013.01); *C07C 253/00* (2013.01); *C07C 253/30* (2013.01); *C07C 253/34* (2013.01)

(58) Field of Classification Search
CPC .... C07C 253/00; C07C 253/30; C07C 253/34
See application file for complete search history.

(56) References Cited

U.S. PATENT DOCUMENTS

| | | | |
|---|---|---|---|
| 2,721,858 | A | 10/1955 | Joyner et al. |
| 2,756,251 | A | 7/1956 | Joyner et al. |
| 2,763,677 | A | 9/1956 | Jeremias |
| 4,364,876 | A | 12/1982 | Kimura et al. |
| 5,624,699 | A | 4/1997 | Lang |
| 6,245,933 | B1 | 6/2001 | Malofsky et al. |

FOREIGN PATENT DOCUMENTS

EP    0459617 A1    12/1991

OTHER PUBLICATIONS

Wu et al., Tetrahedron: Asymmetry (2003), 14(15), 2133-2142}. (Year: 2003).*
Li , Science of Synthesis, 2005, 21, 179-257. (Year: 2005).*
Guseva et al., Russian Chem. Bull., 43, 4, 595 (1994).
Zhong-Liu Wu, et al., "Enantioselective biotransformation of alpha, alpha-disubstituted dinitriles to the corresponding 2-cyanoacetamides using Rhodococcus sp. CGMCC 0497", Tetrahedron: Asymmetry, vol. 14, No. 15, 18 pp. 2133-2142 (2003).
Guseva et al., Russian Chem. Bull., 42, 3, 478 (1993).
W.J. Greenlee, et al., "Mild conversion of carboxamides and carboxylic acid hydrazides to acids and esters", Journal of Organic Chemistry, vol. 46, No. 25, pp. 5351-5353 (1981).
W.H. Mcgregor et al., "Alkaline bromine oxidation of amino acids and peptides: Formation of [alpha]-ketoacyl peptides and their cleavage by hydrogen peroxide", Biochemistry, vol. 1, No. 1, pp. 53-60 (1962).
S.K.S. Senagar et al., "Kinetics and mechanism of copper(II)-catalysed oxidation of asparagine by sodium N-chloro-p-toluenesulfonamide in alkaline media", Journal of the Indian Chemical Society, vol. 65, pp. 88-90 (1988).
Golobolov and Gruber, Russian Chem. Rev., 66, 11, 953 (1997).
Senchenya et al., Russian Chem. Bull., 42, 5, 909 (1993).
G. Laval, et al., "One-pot sequence for the decarboxylation of [alpha]-amino acids", Synlett, No. 4, pp. 542-546 (2003).
PCT International Search Report issued in connection with International Application No. PCT/EP2020/060884 mailed Jul. 14, 2020.

* cited by examiner

*Primary Examiner* — Laura L Stockton
(74) *Attorney, Agent, or Firm* — Steven C. Bauman

(57) ABSTRACT

This invention relates to a process for producing cyanoacetates using asparagine as a precursor to cyanoacetamide, a staring material to form the cyanoacetates.

25 Claims, No Drawings

PROCESS FOR PREPARING CYANOACETATES

BACKGROUND

Field

This invention relates to a process for producing cyanoacetates using asparagine as a precursor to cyanoacetamide, a staring material to form the cyanoacetates.

Brief Description of Related Technology

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624, 699, 4,364,876, 2,721,858, 2,763,677 and 2,756,251. Thus, it is seen one use of cyanoacetates is in the formation of cyanoacrylates.

Vijayalakshmi et al., *J. Ad. Sci. Technol.*, 4, 9, 733 (1990) describes some approaches to the synthesis of cyanoacetates and corresponding cyanoacrylates, including preparation from chloroacetic acid and its esters by subsequent reaction with sodium cyanide.

Guseva et al., *Russian Chem. Bull.*, 42, 3, 478 (1993) describes functionalized cyanoacetates, many of which were used in the subsequent synthesis of corresponding cyanoacrylates. [See also Guseva et al., *Russian Chem. Bull.*, 43, 4, 595 (1994), and Golobolov and Gruber, *Russian Chem. Rev.*, 66, 11, 953 (1997).] Cyanoacetates with siliconised functionalities have been described. See e.g. Senchenya et al., *Russian Chem. Bull.*, 42, 5, 909 (1993) and European Patent Document No. EP 0 459 617.

It would be desirable to find alternative synthetic approaches to making cyanoacetates, particularly if such approaches used readily available and inexpensive starting materials. It would be even more desirable if such approaches generated the subject cyanoacetate in high yield, was readily isolated, and used at least starting materials that are recognized as being safe.

SUMMARY

At a high level, the inventive process provides for the preparation of a cyanoacetate, steps of which comprise:
(a) contacting asparagine with a halogenating agent in an acidic environment to form cyanoacetamide;
(b) optionally, separating therefrom the so-formed cyanoacetamide;
(c) contacting the so-formed cyanoacetamide with an alcohol, in the presence of a mineral acid to form a cyanoacetate;
(d) optionally, separating therefrom the so-formed cyanoacetate. The optional first separation step (step (b)) should yield cyanoacetamide substantially free from the halogenating agent and acid, and by-products. The optional second separation step (step (d)) should yield the cyanoacetate substantially free from the cyanoacetamide, the alcohol, and mineral acid, and by-products. Steps (a) and (c) should be conducted under appropriate conditions and for a time sufficient to yield the cyanoacetamide and the cyanoacetate, respectively.

DETAILED DESCRIPTION

As noted above, the present invention provides a process for the preparation of a cyanoacetate, steps of which comprise:
(a) contacting asparagine with a halogenating agent in an acidic environment to form cyanoacetamide;
(b) optionally, separating therefrom the so-formed cyanoacetamide;
(c) contacting the so-formed cyanoacetamide with an alcohol, in the presence of a mineral acid to form a cyanoacetate;
(d) optionally, separating therefrom the so-formed cyanoacetate. The optional first separation step (step (b)) should yield cyanoacetamide substantially free from the halogenating agent and acid, and by-products. The optional second separation step (step (d)) should yield the cyanoacetate substantially free from the cyanoacetamide, the alcohol, and mineral acid, and by-products. Steps (a) and (c) should be conducted under appropriate conditions and for a time sufficient to yield the cyanoacetamide and the cyanoacetate, respectively.

The cyanoacetate formed by the inventive process may be a $C_{1-20}$ alkyl cyanoacetate, a $C_{6-20}$ aryl cyanoacetate, a $C_{7-20}$ alkaryl cyanoacetate or a $C_{7-20}$ aralkyl cyanoacetate, any of which may be substituted by one or more hydroxyl groups or $C_{1-20}$ alkyl ether groups.

More specifically, the cyanoacetate may be a $C_{1-20}$ alkyl cyanoacetate, where the $C_{1-20}$ alkyl may be straight chain or branched, contain one or more points of unsaturation and may be substituted and/or interrupted by one or more heteroatoms or heteroatom-containing groups (such as trimethylsilyl alkyl, like methyl, ethyl or propyl), or substituted by halogens or substituted or interrupted by halogen-containing groups. For instance, the cyanoacetate may be methyl, ethyl, propyls (like n-propyl or iso-propyl), propargyl, butyls (like n-butyl or iso-butyl), pentyls (like n-pentyl or iso-amyl), hexyl, octyls (like n-octyl or 2-ethylhexyl), nonyl, oxononyl, decyl, dodecyl, allyl, ethynyl, butenyl, cyclohexyl, tetrahydrofurfuryl, chloroethyl, 2,2,2-trifluoroethyl, hexafluoroisopropyl, alkoxy ether alkyl cyanoacetates (such as methoxymethyl, methoxyethyl, methoxybutyl, ethoxyethyl, propoxyethyl, butoxymethyl, or butoxyethyl) and dimethyl siloxane esters of 2-cyanoacetic acid. This recitation is by no means however exhaustive.

The cyanoacetate may also be a $C_{6-20}$ aryl cyanoacetate such as phenyl cyanoacetate.

Or, the cyanoacetate may be a $C_{7-20}$ aralkyl cyanoacetate such as phenethyl cyanoacetate, benzyl cyanoacetate, or toluyl cyanoacetate.

In conducting the process, cyanoacetamide is formed in step (a) from asparagine and then becomes the starting material or precursor to the cyanoacetate.

The asparagine should be used in an amount of about 1 equivalent. The term "equivalent" is intended to capture molar equivalent, whenever it is used herein.

The halogenating agent used in the inventive process may be selected from trihaloisocyanuric acid, N-halosuccinimide, hypochlorites and N-halo-p-toluenesulfonamide salts.

When the halogenating agent is a trihaloisocyanuric acid, the halogenating agent may be selected from tribromoisocyanuric acid or trichloroisocyanuric acid ("TCCA").

When the halogenating agent is a N-halosuccinimide, the halogenating agent may be selected from N-chlorosuccinimide or N-bromosuccinimide.

When the halogenating agent is a hypochlorite, the halogenating agent may be selected from sodium hypochlorite or calcium hypochlorite.

When the halogenating agent is a N-halo-p-toluenesulfonamide salt, the halogenating agent may be a N-chloro-p-toluenesulfonamide sodium salt.

The halogenating agent should be used in an amount of about 0.5 equivalent to about 5 equivalents, such as about 1 equivalent to about 2.5 equivalents, based on 1 equivalent of the asparagine.

The halogenating agent and the asparagine are reacted in an acidic environment. The acidic environment may be created through the addition of an acidic buffer solution. That is, an acidic buffer solution having a pH less than 7 and ordinarily would be made from a weak acid and a salt of a weak acid, such may be the same or different weak acid as the one used. Thus, a citric acid and a sodium citrate salt would be an acidic buffer solution. Desirably, a dibasic sodium phosphate salt may be used in combination with citric acid.

The cyanoacetamide so formed may be separated or used in situ. The yield of the cyanoacetamide should be greater than about 70%, such as approaching quantitative.

When forming the cyanoacetate from the cyanoacetamide, the cyanoacetamide should be used in an amount of about 1 equivalent against which the other reactants may be measured.

An alcohol is used to perform the esterification of step (c). The alcohol chosen may be an alkyl alcohol, an aryl alcohol, an alkaryl alcohol or an aralkyl alcohol. The identity of the chosen alcohol depends on the desired cyanoacetate sought to be prepared. Accordingly, the alcohol may be selected from methanol, ethanol, propanols (such as isopropanol), proparganols, butanols (such as isobutanol), pentanols (such as isoamyl alcohol), hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols (such as methoxymethanol, methoxyethanol, methoxybutanol, ethoxyethanol, propoxyethanol, butoxymethanol, or butoxyethanol), dialkyl siloxanols (such as dimethyl siloxanol or diethyl siloxanol), trialkylsilylalkanols (such as trimethylsilylmethanol, trimethylsilylethanol or trimethylsilylpropanol), should the corresponding respective alkyl cyanoacetate ester sought to be produced. Or, if the chosen alcohol is an aromatic alcohol, such as phenol, benzyl alcohol or derivatives thereof, then the corresponding aryl cyanoacetate ester would be formed.

The alcohol should be used in an amount of about 2.5 to about 25 equivalents, such as about 5 to about 10 equivalents, desirably about 5 to about 7.5 equivalents compared to 1 equivalent of the cyanoacetamide.

The mineral acid used here in the inventive process may be selected from sulfuric acid, sulfurous acid, sulfonic acid, phosphoric acid, phosphorous acid, phosphonic acid, hydrochloric acid or hydrobromic acid.

The mineral acid should be used in an amount of about 0.5 to about 1.5 equivalents to about 1 equivalent of cyanoacetamide, such as in an amount of about 0.6 to about 1.2 equivalents to about 1 equivalent of cyanoacetamide, desirably about 0.6, about 0.9 or about 1.2 equivalents to about 1 equivalent of the cyanoacetamide.

The alcohol should be used in excess to either or both of the cyanoacetamide and the mineral acid.

In the inventive process, the cyanoacetate is formed in a yield of about 70% or greater, such as about 90% or greater.

While the time of reaction is generally given above, the time may be monitored by reference to the formation of the desired product using NMR spectrometry, as noted in the Examples. The time of reaction may be adjusted depending on the identity of the specific reactants, the scale of the reaction and whether heat is added to the reaction conditions.

For the optional steps of (b) and/or (d) appropriate isolation and/or separation techniques may be used to isolate the cyanoacetate.

The following examples are intended to illustrate but in no way limit the present invention.

EXAMPLES

We used reaction conditions reported in J. Le Notre et al., *Green Chem.*, 13, 807-09 (2011) with reference to the oxidative decarboxylation of glutamic acid using N-bromosuccinimide as a halogenating agent and phosphate-saline buffer at a pH of about 5 to form cyanoacetamide, along the synthetic scheme set forth below:

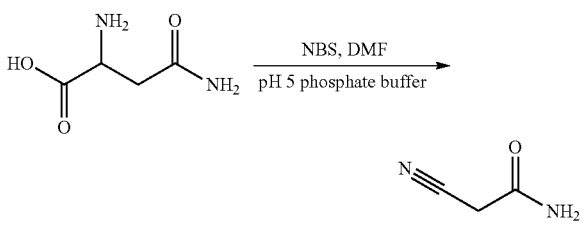

The cyanoacetamide was formed in a yield of about 80%, without isolating the product.

Example 1

To a stirred solution of L-asparagine (3.0 grams, 20 mmol, 1.0 eq) in a pH 5 phosphate buffer (made from citric acid and dibasic sodium phosphate) (90 mL) was slowly added a solution of NBS (10.7 grams, 60 mmol, 3.0 eq) in DMF (20 mL). The reaction mixture was stirred overnight at room temperature and quenched with sodium thiosulfate until colourless. Neat NMR results suggest that the desired product had been formed with a peak at 3.38 ppm and an estimated conversion of about 80%.

Example 2

We used reaction conditions reported in Z.-L. Wu et al., *Tetrahedron: Asymmetry*, 14, 2133-42 (2003) to esterify the amide of cyanoacetamide, along the synthetic scheme set forth below:

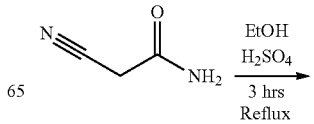

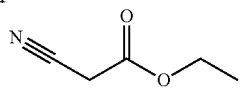

Applying the synthesis conditions of Z.-L. Wu, the ethyl ester of cyanoacetate was obtained. The yields varied, as shown below in Table. The sulfuric acid equivalents were varied as was the time of reaction in the last instance. Table 1 below shows each of the six entries, all having 1 equivalent of cyanoacetamide (30 grams) and 5.75 equivalents of ethanol (94.5 grams).

TABLE 1

| Entry | $H_2SO_4$ (eq) | Time (hrs) | Yield (%) |
|---|---|---|---|
| 1 | 0.3 | 3 | 41 |
| 2 | 0.15 | 3 | 12 |
| 3 | 0.6 | 3 | 69 |
| 4 | 1.2 | 3 | 94 |
| 5 | 0.9 | 3 | 97 |
| 6 | 0.3 | 17 | 32 |

From Entries 3-5, it may be seen that only those having about 70% or higher are within the scope of the inventive process. Thus, the mineral acid range of about 0.6 to about 1.2 is seen to be significant in order to obtain the desired yields.

Confirmation of formation of the ethyl cyanoacetate was obtained by NMR spectral analyses.

What is claimed is:

1. A process for the preparation of a cyanoacetate, steps of which comprise:
   (a) contacting asparagine with a halogenating agent in an acidic environment to form cyanoacetamide;
   (b) optionally, separating therefrom the so-formed cyanoacetamide;
   (c) contacting the so-formed cyanoacetamide with an alcohol, in the presence of a mineral acid to form a cyanoacetate; and
   (d) optionally, separating therefrom the so-formed cyanoacetate, wherein the cyanoacetate is a $C_{1-20}$ alkyl cyanoacetate, wherein the $C_{1-20}$ alkyl may be straight chain or branched, contain one or more points of unsaturation and may be substituted and/or interrupted by one or heteroatoms or heteroatom-containing groups, or substituted by halogens or substituted or interrupted by halogen-containing groups.

2. The process of claim 1, wherein step (a) is conducted for a time sufficient to yield the cyanoacetamide.

3. The process of claim 1, wherein step (c) is conducted for a time sufficient to yield the cyanoacetate.

4. The process of claim 1, wherein step (b) yields cyanoacetamide free from the halogenating agent and acid, and by-products.

5. The process of claim 1, wherein step (d) yields cyanoacetate free from the cyanoacetamide, the alcohol, and mineral acid, and by-products.

6. The process of claim 1, wherein the cyanoacetate is a $C_{1-20}$ alkyl cyanoacetate selected from methyl cyanoacetate, ethyl cyanoacetate, propyl cyanoacetates, butyl cyanoacetates, pentyl cyanoacetates, octyl cyanoacetates, alkoxy ether alkyl cyanoacetates, allyl cyanoacetate, and combinations thereof.

7. The process of claim 1, wherein the halogenating agent is selected from trihaloisocyanuric acid, N-halosuccinimide, hypochlorites and N-halo-p-toluenesulfonamide salts.

8. The process of claim 1, wherein the halogenating agent is selected from tribromoisocyanuric acid or trichloroisocyanuric acid.

9. The process of claim 1, wherein the halogenating agent is selected from N-chlorosuccinimide or N-bromosuccinimide.

10. The process of claim 1, wherein the halogenating agent is selected from sodium hypochlorite or calcium hypochlorite.

11. The process of claim 1, wherein the halogenating agent is N-chloro-p-toluenesulfonamide sodium salt.

12. The process of claim 1, wherein the acidic environment of step (a) is due to the addition of a citric acid buffer.

13. The process of claim 1, wherein the acidic environment of step (a) is due to the addition of a citric acid phosphate buffer.

14. The process of claim 1, wherein the alcohol is an alkyl alcohol, an aryl alcohol, an alkaryl alcohol or an aralkyl alcohol.

15. The process of claim 1, wherein the alcohol is selected from methanol, ethanol, propanols, proparganols, butanols, pentanols, hexanols, octanols, nonanols, oxononanols, decanols, dodecanols, allanol, cyclohexanol, tetrahydrofurfurol, chloroethanol, 2,2,2-trifluoroethanol, hexafluoroisopropanol, alkoxy ether alkanols, dialkyl siloxanols, or trialkylsilylalkanols.

16. A process for the preparation of a cyanoacetate, steps of which comprise:
   (a) contacting asparagine with a halogenating agent in an acidic environment to form cyanoacetamide;
   (b) optionally, separating therefrom the so-formed cyanoacetamide;
   (c) contacting the so-formed cyanoacetamide with an alcohol, in the presence of a mineral acid to form a cyanoacetate;
   (d) optionally, separating therefrom the so-formed cyanoacetate, wherein the alcohol is an aromatic alcohol.

17. The process of claim 1, wherein the alcohol is selected from phenol, benzyl alcohol or derivatives thereof.

18. The process of claim 1, wherein the mineral acid used in step (c) is selected from sulfuric acid, sulfurous acid, sulfonic acid, phosphoric acid, phosphorous acid, phosphonic acid, hydrochloric acid or hydrobromic acid.

19. The process of claim 18, wherein the mineral acid is used in step (c) in an amount of about 0.5 to about 1.5 equivalents to about 1 equivalent of cyanoacetamide.

20. The process of claim 18, wherein the mineral acid is used in step (c) in an amount of about 0.6 to about 1.2 equivalents to about 1 equivalent of cyanoacetamide.

21. The process of claim 1, wherein the alcohol in step (c) is used in excess to either or both of the cyanoacetamide and the mineral acid.

22. The process of claim 1, wherein the cyanoacetate is formed in an amount of about 70% or greater.

23. The process of claim 1, wherein the cyanoacetate is formed in an amount of about 90% or greater.

24. The process of claim 1, wherein step (b) is free from the asparagine, halogenating agents, and by-products.

25. The process of claim 1, wherein step (d) is free from the cyanoacetamide, mineral acid, and/or alcohol, and by-products.

* * * * *